United States Patent [19]

Jalbert

[11] Patent Number: 5,372,221
[45] Date of Patent: Dec. 13, 1994

[54] ACTIVE BRAKE SENSOR

[75] Inventor: Vincent P. Jalbert, Middlebury, Conn.

[73] Assignee: Otis Elevator Company, Farmington, Conn.

[21] Appl. No.: 916,918

[22] Filed: Jul. 20, 1992

[51] Int. Cl.$^5$ .............. F16D 66/00; G01L 5/28; B60T 17/18

[52] U.S. Cl. .................... 188/1.11; 73/130; 303/91; 340/454

[58] Field of Search .............. 188/1.11, 181 A, 181 R, 188/187; 303/91; 73/130, 518, 597; 340/453, 454, 466

[56] References Cited

U.S. PATENT DOCUMENTS

| | | | |
|---|---|---|---|
| 3,815,426 | 6/1974 | Rohner | 73/518 X |
| 3,905,235 | 9/1975 | Shaw | 73/518 X |
| 4,266,633 | 5/1981 | Barabino et al. | 188/1.11 |
| 5,009,103 | 4/1991 | Sato et al. | 73/597 |
| 5,038,615 | 8/1991 | Trulson et al. | 73/597 |
| 5,062,298 | 11/1992 | Falcoff et al. | 73/597 |
| 5,228,342 | 7/1993 | McShane | 73/597 |

Primary Examiner—Robert J. Oberleitner
Assistant Examiner—Alfred Muratori

[57] ABSTRACT

An ultrasonic wave is propagated through a brake pad to determine various brake conditions including brake pad wear, brake status (engaged/disengaged), a wet brake failure or a brake drag failure. The propagation and reflection time of an echo signal generated at a far boundary of the pad is indicative of brake wear. Brake drum or disc speed is determined by using radial indicia on the periphery of the drum or disc to modulate an ultrasonic wave reflected from or transmitted through the drum or disc and demodulating the sensed modulated signal as a speed indication. The various other conditions are determined by means of filters, comparators and logic.

13 Claims, 8 Drawing Sheets

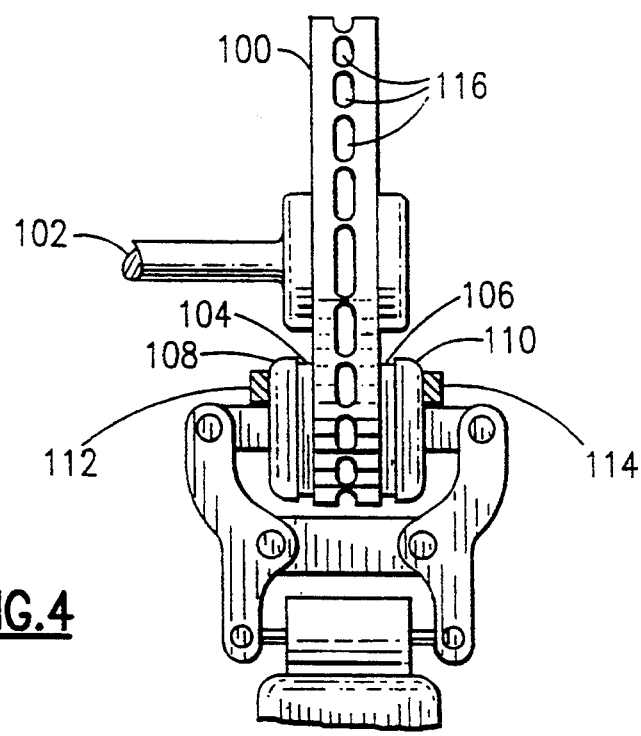
FIG. 4
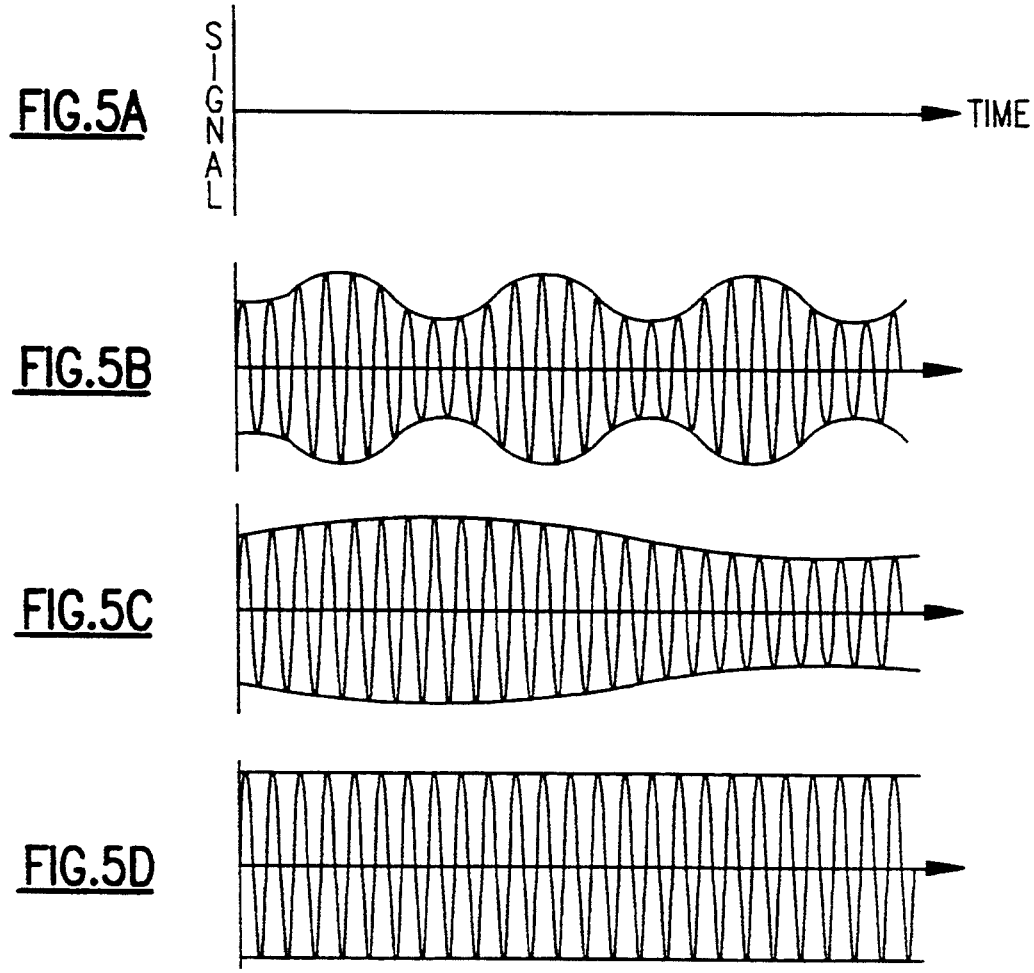
FIG. 5A
FIG. 5B
FIG. 5C
FIG. 5D

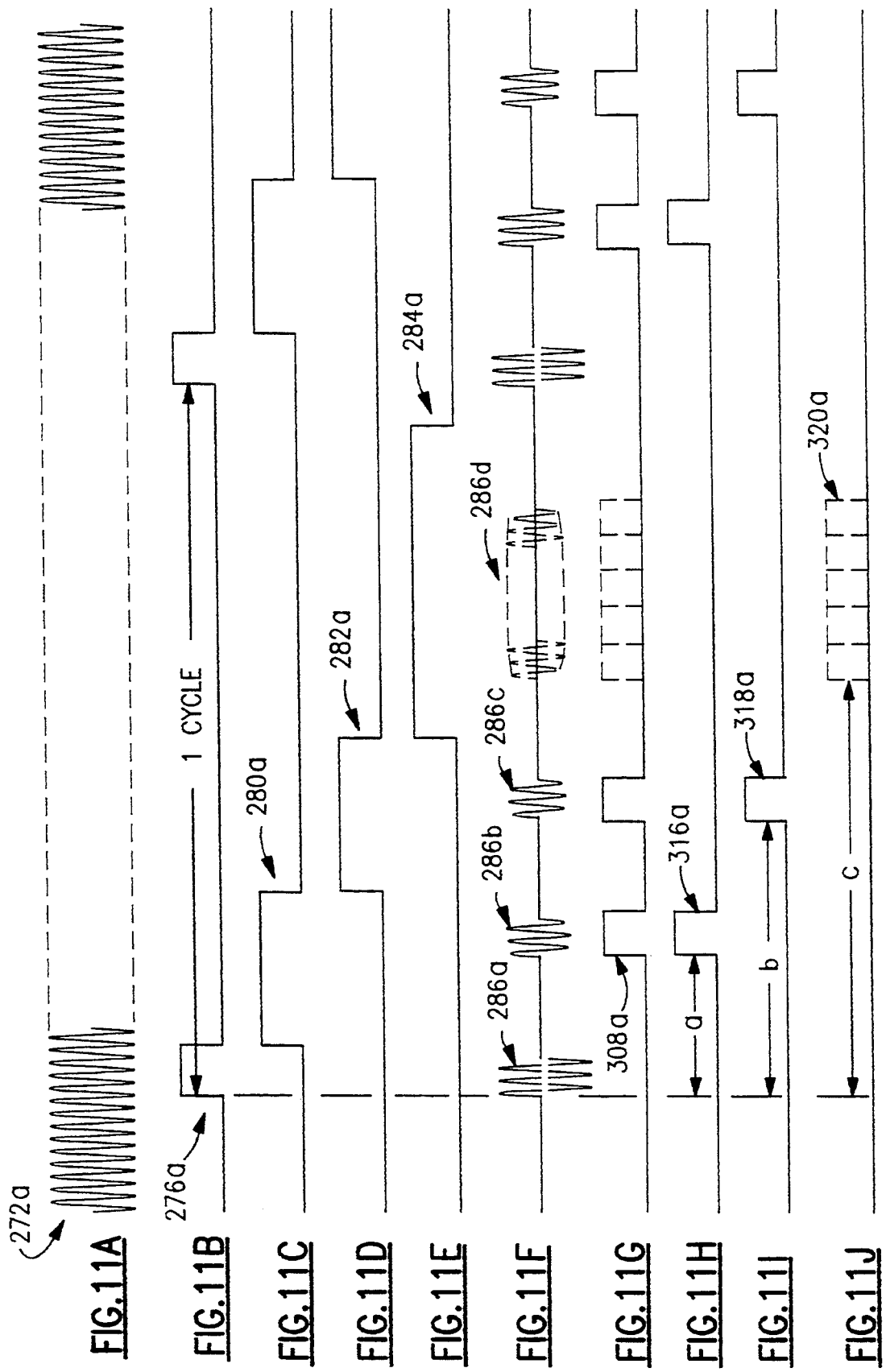

ACTIVE BRAKE SENSOR

TECHNICAL FIELD

This invention relates to brakes, and more particularly, to an active sensing method for brake systems and apparatus.

BACKGROUND OF THE INVENTION

Brake failures, conditions and capacity have been measured before by passive temperature sensors, passive ultrasound sensors, etc., as shown for example in U.S. Pat. No 4,591,213. See also for example column 8, lines 6-19 of U.S. Pat. No. 4,743,074 to Inoue which shows a control system which includes the use of passive ultrasonic sensors. Its main function is to prevent audible brake squeal. Vibrations and brake force are also measured. Details on ultrasound sensors may be found in Siemens publication "Ultrasonic Remote Sensors for Noncontact Object Detection" by Kleinschmidt and Magori, reprinted from "Siemens Forsch.-u. Entwickl.-Ber." Vol. 10 (1981) No. 2, pp. 110-118.

However, these systems are relatively complex, and generally are not particularly reliable. In a passive ultrasound system, a fault condition is detected by sensing vibrations within the system; however, if the sensor fails, the fault will go undetected.

In elevator systems, as another example, switches have been used to determine the status of the brake. When the elevator car is landing at a floor, the drive system is still active. It would be desirable to determine at this point if the brake will be capable of working, i.e., ahead of time. This must be done with no load on the brake because the car may be at or near balanced load. This cannot be done with a friction force measuring sensor or any other of the current methods. A switch won't give an indication if the brake has dropped but only if one of the linkages has moved enough to cause activation of the mechanical switch. This arrangement will not detect several failure conditions, such as worn pad, misaligned shoes/pads, missing shoes/pad or linkage failures. The switch doesn't measure force, but only displacement of the linkage.

DISCLOSURE OF INVENTION

The object of the present invention is to provide an active brake sensing apparatus and method.

According to the present invention, an ultrasonic wave is provided for transmission through a brake shoe, and pad and, in some cases, a rotating member, and either the transmitted ultrasonic wave or its reflection is sensed and a brake status signal is provided in response thereto.

The present invention provides an active ultrasound brake sensing system to measure braking ability. This system is comprised of an active brake sensor circuit and one or more ultrasound transducers which are attached to the brake shoe or shoes. In its simplest form, ultrasound energy may be transmitted continually from a transducer. This energy passes through the brake assembly to reach another transducer or to echo back to the transmitting transducer for sensing. The amount of energy received is directly proportional to the level of braking ability. This is due to the fact that the braking ability and the ability to transfer ultrasound energy are both a function of surface area, contact and force against the rotating member.

The active sensor circuit's main functions are to generate and transmit an ultrasound signal, to receive and filter the receive signal and to compare the receive signal to a known standard to report its condition.

In further accord with the present invention, the sensed signal is compared to a reference signal having a magnitude indicative of a reduced friction condition and in response to the sensed signal magnitude increasing greater than the reference value, a brake failure signal is provided indicating that the brake is wet.

Brakes can also fail due to unintended lubrication, such as in the case when the brake gets wet. Any type of fluid that can cause reduced friction, will also cause an increase in ultrasound energy transfer. Therefore, a marked increase in signal strength will also represent a brake failure.

In still further accord with the present invention, the sensed signal is compared to a reference signal having a magnitude indicative of a high vibration condition such as might be caused by brake drag.

Another important feature of this system is that when the brake is lifted (OFF) the system may listen for unusual vibrations, such as might be caused by brake drag. By early detection of continuous brake drag, most serious brake failures may be prevented.

Further to the present invention, by measuring the time of flight for the ultrasound signal or its echo brake pad wear may also be measured. Moreover, temperature effects may be taken into account by measuring the thickness of the shoe using ultrasound time of flight as well.

In further accord with the present invention, wheel speed may be measured when the brake is engaged by providing an ultrasound wave for modulation by radial indicia on a brake drum or disc, sensing the modulated wave and demodulating the sensed signal.

This system can be applied to either drum or disc brakes. Its application is not limited to any particular system and can be used for example in elevator systems, automobiles, aircraft, etc.

The present invention provides, for the given level of information, a relatively simple method of measuring braking capacity independent of load, as would be the case when the drive is still on or for a balanced load, the ability to detect wet or otherwise lubricated brakes, the ability to measure wheel speed and the ability to provide diagnostic information such as pad wear and brake drag.

These and other objects, features and advantages of the present invention will become more apparent in light of the detailed description of a best mode embodiment thereof, as illustrated in the accompanying drawing.

BRIEF DESCRIPTION OF THE DRAWING

FIG. 4 shows a disc brake having an active sensor, according to the present invention, for sensing wheel speed;

FIG. 5 shows some signals, according to the present invention, related to the system of FIG. 4;

FIG. 11 shows some of the signals of FIG. 10, according to the present invention.

BEST MODE FOR CARRYING OUT THE INVENTION

Figure 1:
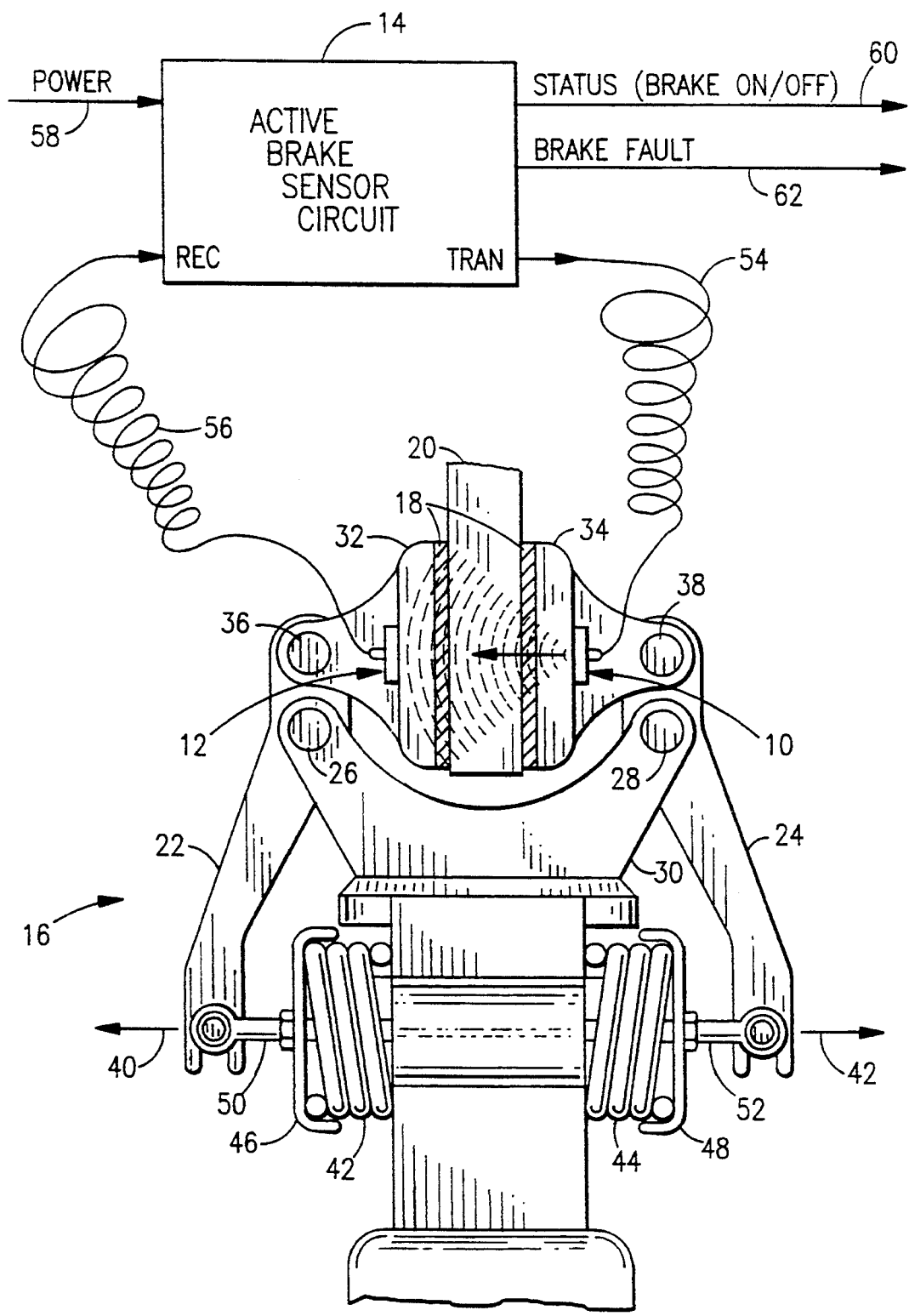
FIG. 1 is an illustration of a disc brake system having an active brake sensor and circuit, according to the present invention.

FIG. 1 shows an ultrasound transmitter 10, and ultrasound receiver 12 and an active brake sensor circuit 14 which together comprise a system for measuring, among other things according to the present invention, the braking ability of a brake, such as a disc brake 16 having pads 18 for being pressed against the surfaces of a rotating disc 20, the edge of which is shown in FIG. 1. The brake 16 has pivot arms 22, 24 which pivot on pivot points 26, 28, respectively, mounted on a yoke 30. The pivot arms 22, 24 cause the brake pads 18 to be pressed against the disc 20 by means of brake shoes 32, 34 attached to the pivot arms 22, 24 at pivot points 36, 38. The pivot arms 22, 24 are normally forced, respectively, in directions 40, 42 by means of a spring force provided, respectively, by springs 42, 44 pressing against holders 46, 48 attached to independent rods 50, 52. The rods 50, 52 are independently actuable in directions opposite to the directions 40, 42 to pull the lever arms 22, 24 in such a direction as to release the brake pads 18 from the surface of the disc 20 thereby lifting the brake. It is a fail safe brake in that if the actuation power is removed, the springs will cause the brake to engage.

The present invention is, however, not particularly directed towards the type of brake used but the active brake sensor 10, 12 and its signal processing circuitry 14. Indeed, the present invention may be used on a drum brake as well, as shown in another embodiment below.

In the system of FIG. 1, ultrasound energy may be transmitted on a signal line 54 from the circuit 14 to the transmitter 10 which may be an ultrasound transducer. Energy generated by the transducer 10 passes through the brake shoe 34 and its associated brake pad 18, the disc 20 and the brake shoe 32 with its associated pad 18. The receiver 12, which may be an ultrasound transducer, senses the magnitude of the ultrasound energy received and provides a signal having a magnitude indicative thereof on a line 56 to the circuit 14.

According to the present invention, the amount of energy that is received by the transducer 12 is directly proportional to the level of braking ability. This is due to the fact that the braking ability and the ability to transfer ultrasound energy are both a function of surface area contact and force against the rotating member.

The active brake sensor circuit 14 has the following functions:

1. To generate and transmit the ultrasound signal on the line 54,
2. To receive and filter the signal on line 56,
3. To compare the received signal to a known standard and report its condition (on, off, or fault).

The circuit 14 is powered by a power signal on a line 58 and provides a status signal (BRAKE ON/OFF) on a line 60 and a brake fault signal on a line 62. The nature of the brake fault signal will be described below.

Figure 2:
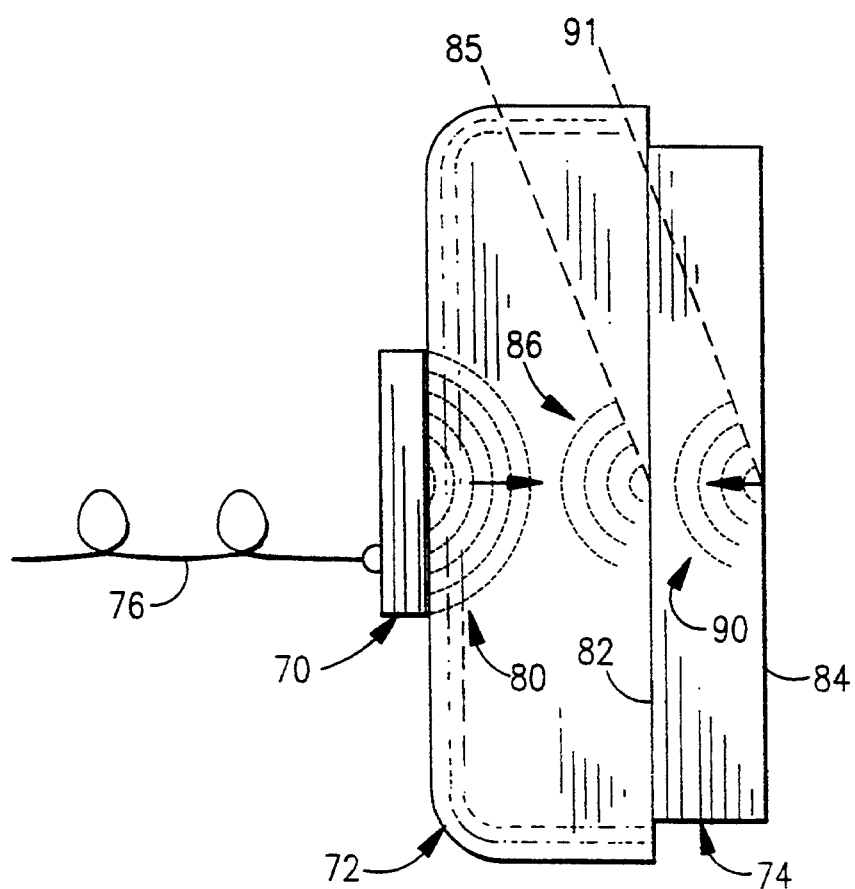
FIG. 2 is an illustration of an active brake sensor, according to the present invention, for sensing brake wear and temperature.

Turning now to FIG. 2, an ultrasound transducer 70 is shown mounted on a brake shoe 72 having a brake pad 74 attached thereto. The transducer 70 is energized by a signal on a line 76 having a transmit pulse wave form 78 as shown for example in FIG. 3 transmitted as illustrated by a wave front 80 propagating from left to right in FIG. 2 from the transducer 70 to an interface 82 between the brake shoe 72 and the brake pad 74 at which point the propagating wave front 80 is both reflected to some extent and propagated on through the brake pad to a second interface 84 at the opposite surface of the brake pad 74 where the propagating wave front is again reflected. The first reflection is signified occurring at a point 85 by a wave front 86 propagating from right to left and as further illustrated in FIG. 3 by a wave form 88 received at the transducer 70 which may be provided on the line 76 to a signal processing circuit where the time of propagation from the transducer 70 to the interface 82 and back again is signified by a time "a". A wave front 90 signifies propagation of the second reflection back toward the transducer and is also signified by a waveform 92 in FIG. 3 which is sensed at the transducer 70 after a propagation and reflection time "b" in FIG. 3.

Thus, the transducer 70 mounted on the back of the brake shoe 72 acts both as a transmitter and a receiver of ultrasound energy. Operating like a radar system, the transducer will routinely transmit a burst of energy and then switch to the receive mode to listen for echoes. The first echo 88 shown in FIG. 3 will result from the interface 82 of the brake shoe and the brake pad. The time a between the start of the transmission and the arrival of the first echo will be constant except for variations caused by temperature. Therefore, variation in the time measurement "a" will have a direct relation to temperature changes in the shoe 72. Since it is necessary to know the temperature in order to determine the speed of sound in the materials, this is a very useful measurement.

The second echo 92 that is received will result from the outside surface 84 of the brake pad 74. The time "b" between the start of the transmission and the arrival of the second echo will vary both with temperature and pad thickness. The time variations in the "b" measurement caused by temperature changes can be compensated for based upon the data from the "a" measurement. After adjusting the "b" measurement for temperature, this measurement will represent the distance from the transducer to the outside surface of the brake pad. As the thickness of the brake shoe is known and will not change (the effects of material expansion on the thickness of the brake shoe are small enough to be neglected) then the compensated "b" measurement can be used as a measure of pad thickness.

Referring now to FIG. 4, a disc brake is shown for engaging a rotor 100 shown edgewise in the figure and rotated by a shaft 102. The brake has opposing brake pads 104, 106 mounted to associated brake shoes 108, 110, respectively. On each shoe is mounted an ultrasonic transducer 112, 114, respectively.

When a brake is engaged, it is possible to measure wheel speed for the purpose of feedback or control. Generally, this measurement would be more accurate with a different operating mode from the method just described for measuring pad thickness. However, one system could easily handle both operating modes.

FIG. 4 represents this system implemented on a disc brake system and FIG. 5 represents the signals for different operating conditions. A key element of this system is that the rotor 100 has evenly spaced voids or vent holes 116 that are aligned under the brake pads and normally provided for cooling purposes. Vent holes are typically provided for cooling purposes and would fill this requirement. One of the transducers 112, 114 functions as a transmitter and the other functions as a receiver. The transmitter continuously transmits an ultrasound signal.

When the brake is disengaged, the level of the signal that is received will be so low as to be considered no signal at all, as shown in FIG. 5(a). This lack of signal will result from the air gaps between the rotor and brake pads. Depending on the mechanical arrangement, some energy may be received via the linkage. This undesired signal will have a significant phase shift from the transmission signal, as compared to a direct signal. This phase shift will make it easy to filter out this unwanted signal.

When the brake is engaged and the rotor is still moving, due to the large contact area and the pressure applied to the brake pads, most of the ultrasound energy will pass through the rotor and be received by the second transducer. The amplitude of the received signal will be reduced by the voids in the rotor as they pass by. The received signal will be amplitude modulated by the voids or vent holes. The wheel speed (in revolutions per second) will be equal to the modulation frequency divided by the number of vents. As shown in FIG. 5(b), the brake is engaged and the rotor is turning at relatively high speed as compared to the relatively low speed sensed as shown in FIG. 5(c).

When the brake is engaged and stopped, the amplitude of the received signal will be constant, as indicated in FIG. 5(d), indicating no motion.

This system would also work in a reflective mode. In the case of a drum brake the reflective mode would be more appropriate. It is typical to find ridges on the outside surfaces of brake drums, also for cooling purposes which may be employed effectively for the purposes disclosed herein.

Figure 6:
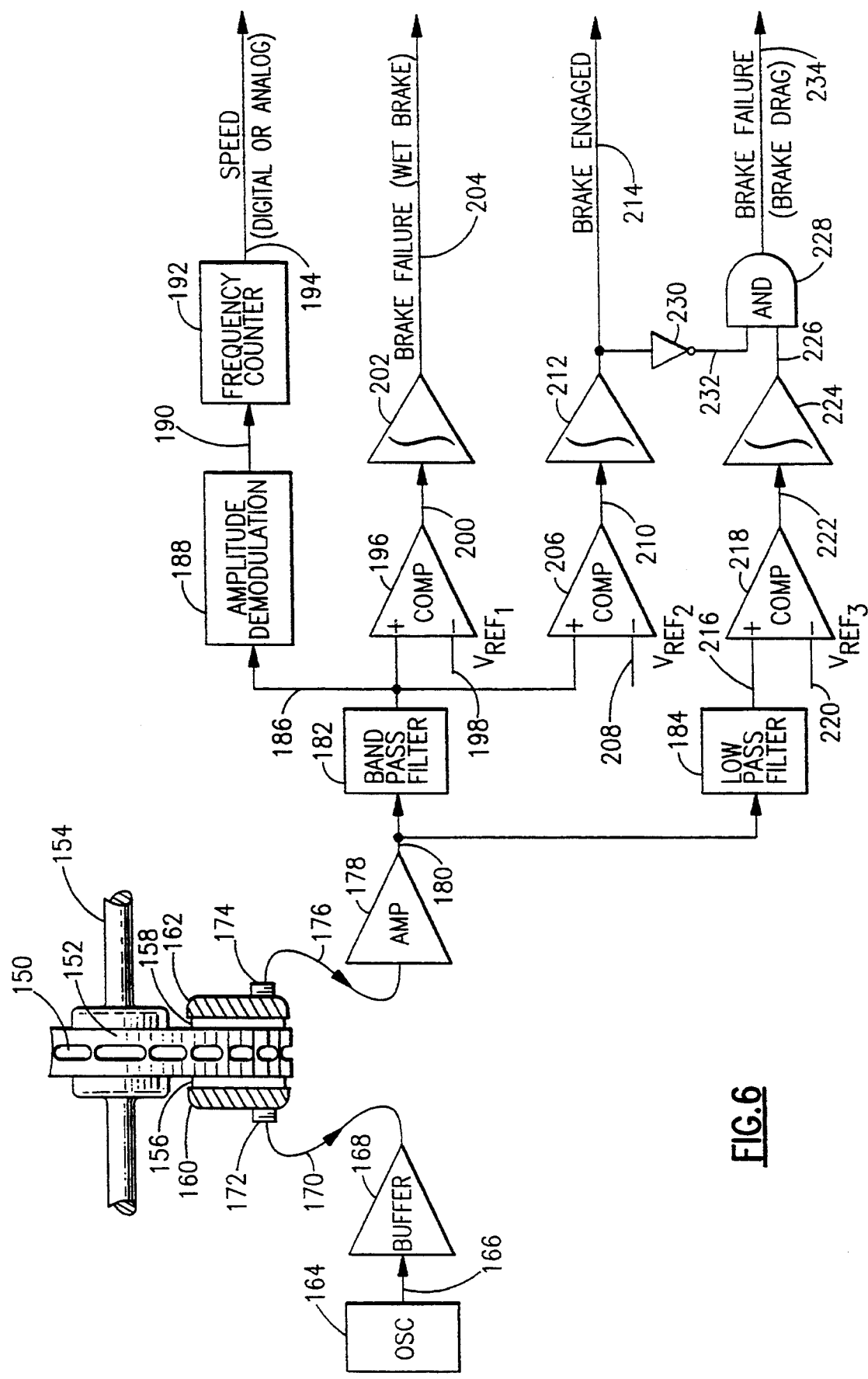
FIG. 6 shows, according to the present invention, an active sensor and signal processor for providing signals indicative of speed, brake engaged, brake failures including a wet brake, brake drag and a lack of braking force.
Figure 7:
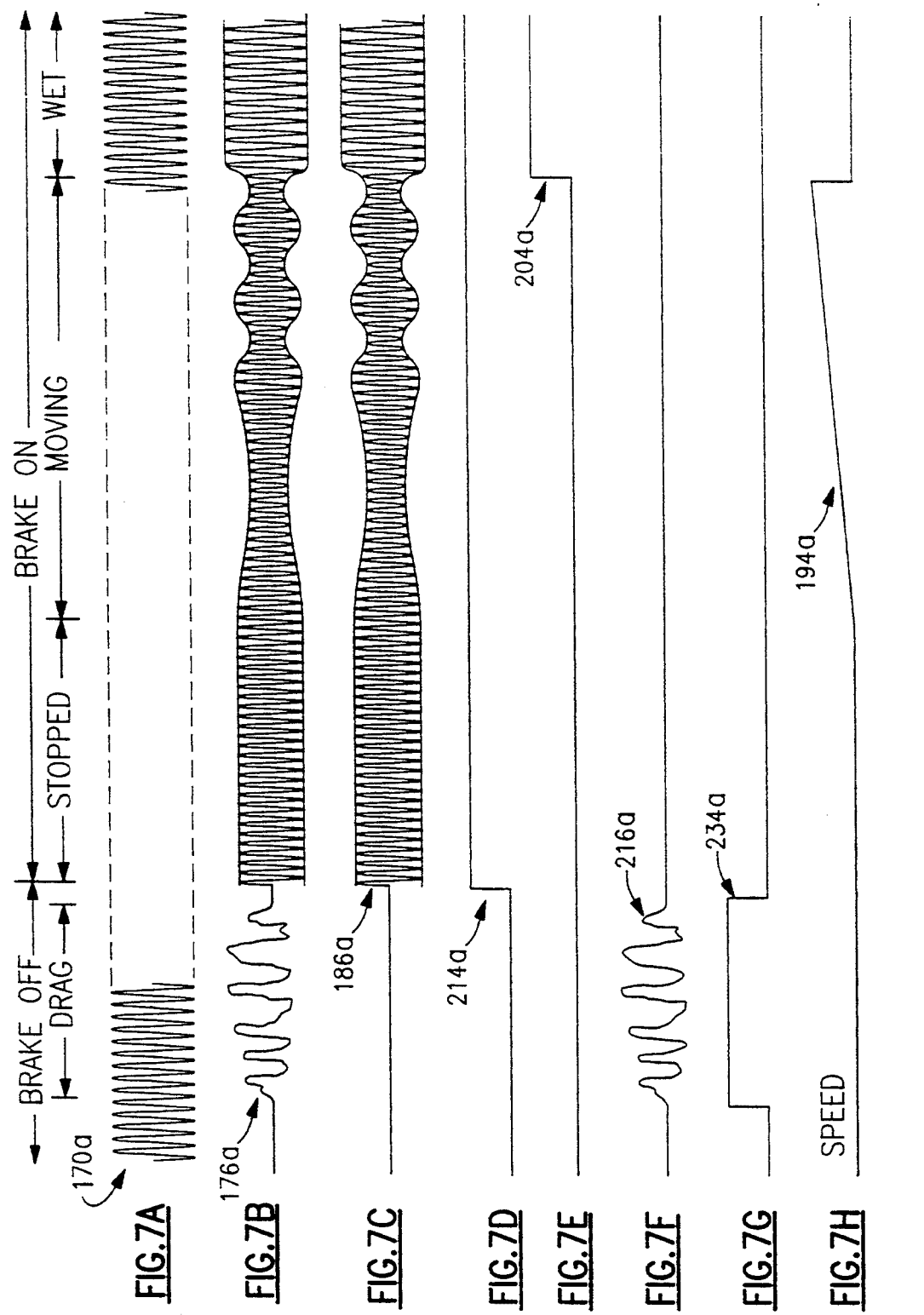
FIG. 7 shows some of the signals of FIG. 6, according to the present invention.

A circuit shown in FIG. 6 with accompanying wave forms in FIG. 7 accomplishes the speed measurement technique of FIGS. 4 and 5 and, in addition, the brake fault function and the brake status function described in connection with FIG. 1. The brake pad thickness determination function as described in connection with FIGS. 2 and 3 will be described subsequently in connection with an embodiment for a drum brake.

In FIG. 6, a disc brake is again shown similar to that shown in FIG. 4 having vents 150 in a disc 152 rotated by a shaft 154 and braked by brake pads 156, 158 as actuated by brake shoes 160, 162. The actuation means are not shown. An oscillator 164 provides an oscillation signal on a line 166 to a buffer 168 which in turn provides a buffered oscillating signal on a line 170 as shown by a wave form 170a in FIG. 7(a) to an ultrasound transducer 172 which, in response to the buffered oscillating signal provides an ultrasonic wave through the shoe 160, the brake pad 156, the disc 152, the brake pad 158 and the brake shoe 162 which may be sensed by an ultrasound sensor 174 which provides a sensed signal on a line 176 as shown by a wave form 176a in FIG. 7(b) to an amplifier 178 which amplifies the sensed signal and provides an amplified sensed signal on a line 180 to a bandpass filter 182 and a low pass filter 184. The purpose of the bandpass filter is to exclude any undesired signals (vibrations) and provides a bandpass filtered signal on a line 186 as shown by a wave form 186a in FIG. 7(c) to an amplitude demodulation circuit 188 which performs demodulation of the signal on the line 186 which may take the form as shown for example in any of the figures of FIG. 5, in order to provide a demodulated signal on a line 190 to a frequency counter 192 which in turn provides an analog or digital speed signal on a line 194 as shown by a wave form 194a in FIG. 7(h) having a magnitude indicative of the angular velocity of the rotating disc 152.

The bandpass filtered signal on the line 186 is also provided to a comparator 196 which compares the magnitude of the signal on the line 186 to a reference signal 198 ($V_{ref1}$) and provides a signal on a line 200 in the event the signal on the line 186 compares to the signal on the line 198 in such a way that it indicates with a higher than normal signal that increased energy transfer is occurring, such as occurs with a wet brake. The signal on the line 200 is provided to an integrator 202 which in turn provides a brake failure signal on a line 204 as shown by a wave form 204a in FIG. 7(e) indicative of a wet brake condition. The selection of the magnitude of the signal on the line 198 is made based on measured energy transfers for each type of mechanism.

The signal on the line 186 is also provided to a comparator 206 for comparison with a reference signal on a line 208 ($V_{ref2}$) having a magnitude selected on the basis of measured energy transfer for normal operation. In the event of a comparison indicative of a selected level of energy transfer, a signal on a line 210 is provided to an integrator 212 for providing a brake engaged signal on a line 214 as shown by a wave form 214a in FIG. 7(d) meaning that the received energy level is consistent with a normal brake engagement. The amplified sensed signal on the line 180, as mentioned, is also provided to the low-pass filter 184 which in turn provides a low-pass filtered signal on a line 216 as shown by a wave form 216a in FIG. 7(f) such as shown in FIG. 7(f) by a wave form 216(a). A comparator 218 is responsive to the signal on the line 216 and a reference signal on a line 220 having a magnitude selected according to empirically determined safe levels of vibration energy. In the event of a comparison between the signals on the lines 216 and 220 indicating an unsafe level, the comparator 218 provides a signal on a line 222 to an integrator 224 which in turn provides a signal on a line 226 to an AND gate 228. An inverter 230 is responsive to the brake engaged signal on the line 214 and provides an inverted brake engaged signal on a line 232 to the AND gate 228. In the event that the brake is not engaged and there is an indication from integrator 224 of a higher than normal level of vibration present in the system, then the AND gate 228 provides a brake failure signal on a line 234 as shown by a waveform 234a having a magnitude indicative of a brake drag condition.

Figure 8:
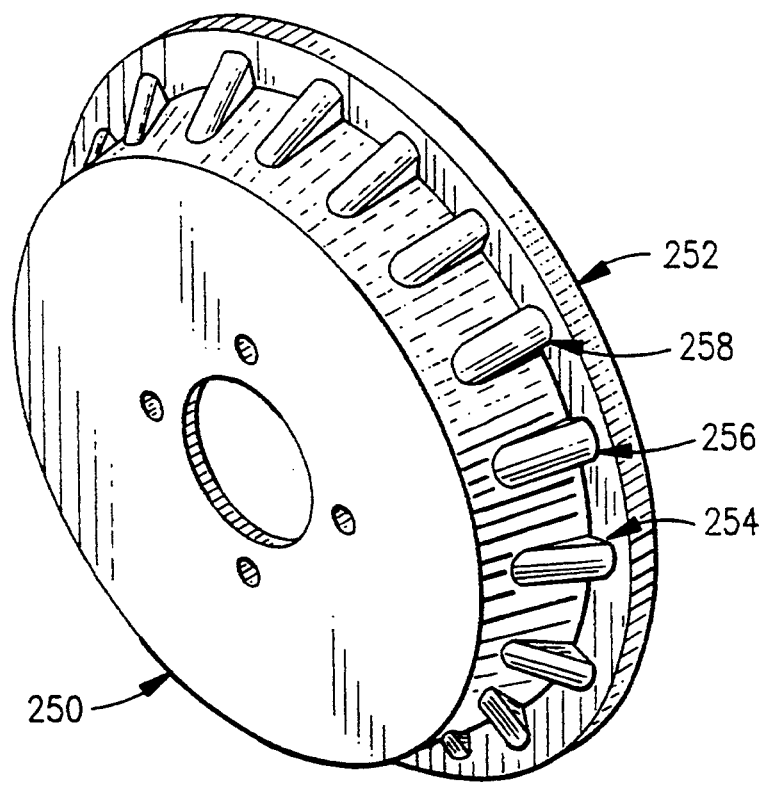
FIG. 8 shows a brake drum for use, according to the present invention.
Figure 9:
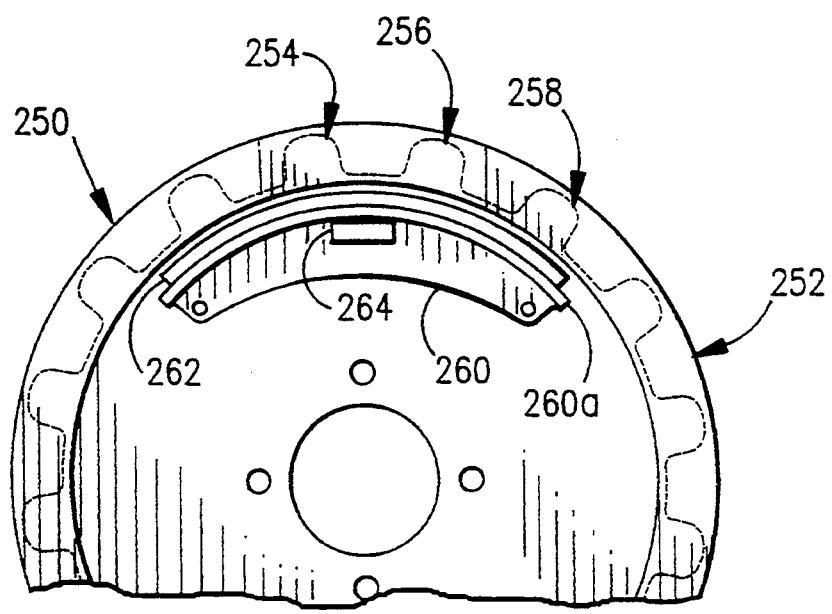
FIG. 9 shows an inside view of the brake drum of FIG. 8, according to the present invention, having an active sensor for sensing speed.

Turning now to FIG. 8, a brake drum 250 is shown having a flange 252 and a plurality of ribs 254, 256, 258, etc., along the periphery of the drum and flange 250, 252. A brake shoe 260 in FIG. 9 is shown having a brake pad 262 mounted thereon inbetween the shoe and an inner face of the drum 250. The actuation means is not shown. An ultrasound transducer 264 is shown mounted to the brake shoe 260 in a position that will enable it to transmit and receive ultrasonic waves in the manner already discussed in connection with FIGS. 2 and 3.

Figure 3:
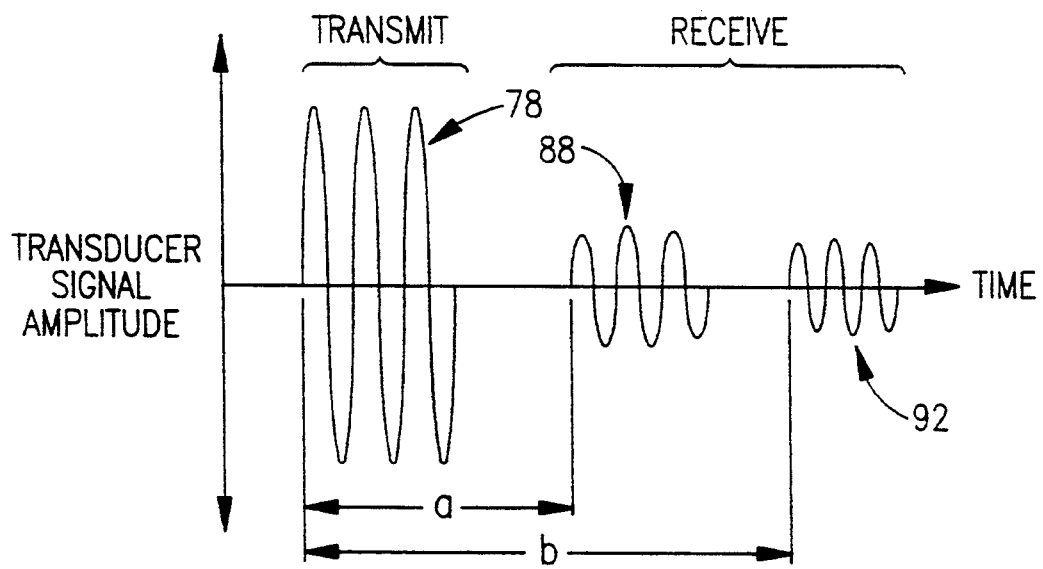
FIG. 3 is an illustration of a transmit signal and a receive signal, according to the present invention, as utilized in the active brake sensor of FIG. 2.
Figure 10:
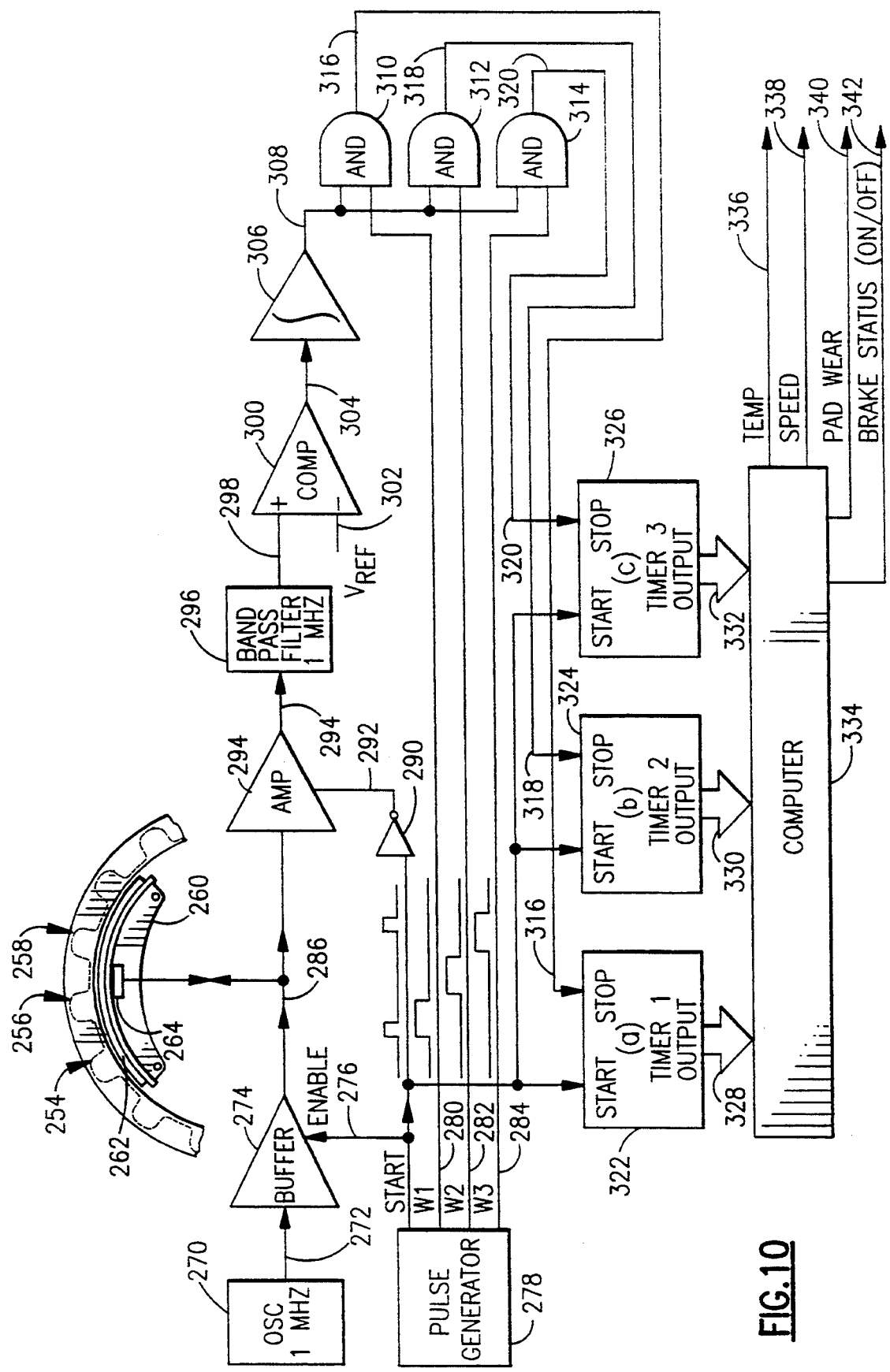
FIG. 10 shows a circuit which may be used, according to the present invention, in connection with the active sensor of FIG. 9.

A circuit which is capable of carrying out the functions described already in connection with FIGS. 2 and 3 on the brake drum of FIGS. 8 and 9 is shown in FIG. 10. There, the transducer 264 is shown along with the brake shoe 260, the brake pad 262 and the ribs 254, 256, 258 on the brake drum 250. An oscillator 270 provides a 1 MHz oscillating signal on a line 272 to a buffer 274 which is enabled by a start signal on a line 276 from a pulse generator 278. The oscillating signal on the line 272 is shown in a wave form 272a in FIG. 11(a). The start signal on the line 276 is shown by a wave form 276a in FIG. 11(b). It is shown as having a one cycle period of an unspecified time but which may be on the order of 20 microseconds, for example. The pulse generator 278 also provides three window signals on line 280, 282, 284 as shown, respectively, by wave forms 280a, 282a, 284a, in FIG. 11(c), (d) and (e). These window signals are timed to successively cover the cycle of the enable signal on the line 276, as shown in FIG. 11. Their purpose is to stop signals to the timers that time the echo signals to be described subsequently.

The buffer 274 provides a transmit signal on a line 286 as shown by a transmit wave form 286a as shown in FIG. 11(f) during the pulse 276a of the enable signal on the line 276. It will be recalled from FIG. 2, that such a pulse will result in a ultrasonic wave front such as the wave front 80 of FIG. 2 propagating through the brake shoe to a boundary 82 where it will be reflected back to the transducer where it may be sensed as an echo signal as shown, for example, in FIG. 11(f) by a wave form 286b. With the knowledge of the thickness of the particular brake shoe 260 flange 260a, the approximate return time of the echo will be known and the timing of its return can be very precisely approximated so that a timer "window" 280a can be provided which would be slightly longer than necessary for the longest propagation and reflection back time, given the thickness of the shoe flange. This echo is used to measure the temperature of the shoe. It will also be recalled from FIG. 2 that part of the propagating way front 80 will not be reflected and will instead be propagated on through the brake pad 262 where it will be reflected again at the boundary between the brake drum and the surface of the brake pad or the brake pad and the air gap. This second echo is used to measure the time to determine the pad wear. It is shown by a wave form 286c in FIG. 11(f). Both the echoes 286b, 286c are used, along with their associated window signals, to stop their respective timers, as described in more detail below.

An additional echo signal as shown by a wave form 286d is shown in FIG. 11(f) and represents the time for a third echo used to determine if the brake is engaged and if it is, the wheel speed is also measured in a manner similar to that already described in connection with the disc brake embodiment.

An inverter 290 is responsive to the start signal on the line 276 and provides an inverted start signal on a line 292 to an amplifier 294 which is also responsive to the echo signals on the line 286 for providing an amplified echo signal on a line 294 but only when enabled by the signal on the line 292. A bandpass filter (1 MHz band from 0.5 MHz to 2 MHz) filters the signal on the line 294 and provides a bandpassed signal on a line 298 to a comparator 300 which compares the magnitude of the signal on the line 298 to the magnitude of a reference signal on a line 302 indicative of a minimum threshold for a valid echo signal (as opposed to a noise signal) and in the event of a comparison indicating that it is a valid echo signal, provides a signal on a line 304 to an integrator which integrates the signal on the line 304 and provides an integrated signal on a line 308 to a plurality of AND gates 310, 312, 314 which are also responsive, respectively, to the window signals on the lines 280, 282, 284 already discussed in connection with the wave forms 280a, 282a and 284a. The signal on the line 308 is illustrated in FIG. 11(g) by a wave form 308a which is generated by the previously described circuitry. In response to the signal on the line 308 and the window signal on the line 280, the AND gate 310 provides a signal on a line 316 as illustrated by a wave form 316a in FIG. 11(h). The AND gate 312 provides a signal on a line 318 as illustrated by a wave form 318a in FIG. 11(i). The AND gate 314 provides a signal on a line 320 as illustrated by a wave form 320a in FIG. 11(j). The use of these signals will be described in more detail below in connection with a first timer 322 for timing the first echo to determine the brake temperature, a second timer 324 which measures the time for the second echo to determine the pad wear and a third timer 326 to measure the time for the third echo to determine if the brake is engaged, as well as the speed.

As shown in FIG. 10, the timers 322, 324, 326 are all responsive to the start signal on the line 276 at the beginning of each cycle in order to commence timing. The first timer 322 is responsive to the stop signal on the line 316 for stopping after an elapsed time "a" as shown in FIG. 11(h) upon the occurrence of the leading edge of the pulse 316a. The timer 322 provides an output indicative of the timing of the first echo 286b and is used to determine the brake temperature per the following equation.

$$a = S_s \cdot K_s \cdot \text{Temp} \cdot 2 \cdot D_s$$

or $$\text{Temp} = \frac{a}{S_s \times K_s \times 2 \times D_s},$$

Where temp: temperature,
a: Round trip flight time for the first echo.,
$S_s$: Speed of sound in the brake shoe at 25° C.,
$K_s$: The temperature coefficient for the speed of sound in the brake shoe, and
$D_s$: The thickness of the brake shoe.

The second timer 324 is responsive to the stop signal on the line 318 for measuring the time for the second echo 286c in order to determine the pad wear per the following equation:

$$b = a + (S_p \cdot K_p \cdot \text{Temp} \cdot 2 \cdot D_p)$$

or $$D_p = \frac{b - a}{S_p \times K_p \times \text{Temp} \times 2},$$

Where temp: temperature,
b: Round trip flight time for the second echo, $S_p$: Speed of sound in the brake pad,
$K_p$: The temperature coefficient for the speed of sound in the brake pad, and
$D_p$: The thickness of the brake pad.

The third timer 326 is responsive to the stop signal on the line 320 for measuring the time of the third echo 6(d) to determine if the brake is engaged and, if it is, the wheel speed is also measured. The third echo will only appear if the brake is engaged. If the brake is engaged and the wheel is moving, the arrival time for the third echo will vary between two limits. These limits are set by the peaks and valleys of the ridges on the brake drum. The third echo is reflected off the outside edge of the brake drum. The third echo measures the thickness of the brake drum as it is moving. The speed is represented by the rate of change of the drum's thickness.

$$\text{Wheel Speed (Rev/Sec)} = \frac{1}{\text{cycle time} \times \text{number of ribs}},$$

Where cycle time is the time between peak thickness reading from the third echo.

Although the invention has been shown and described with respect to a best mode embodiment thereof, it should be understood by those skilled in the art that the foregoing and various other changes, omissions, and additions in the form and detail thereof may be made therein without departing from the spirit and scope of the invention.

I claim:

1. A brake sensing method, comprising the steps of:
   providing an oscillating electrical signal (54);
   providing, in response to the oscillating electrical signal, an ultrasonic wave for transmission through a brake shoe and pad;
   providing, in response to the transmitted ultrasonic wave or a reflection thereof, a sensed electrical signal (56); and
   providing, in response to the sensed electrical signal, a brake on/off status signal (60) or a brake fault signal (62) indicative of a brake drag condition or a wet brake condition.

2. A brake sensing apparatus, comprising:
   an active brake sensor circuit, responsive to an electrical power signal and to a sensed electrical signal having a magnitude indicative of ultrasonic energy transmitted through a pair of brake pads, for providing an electrical excitation signal and an electrical status signal having a magnitude indicative of brake on/off status;
   a first ultrasonic transducer, responsive to the electrical excitation signal, for providing the ultrasonic energy transmitted through the pair of brake pads; and
   a second ultrasonic transducer, responsive to the ultrasonic energy transmitted through the pair of brake pads, for providing the sensed electrical signal.

3. A method for sensing wear of a brake pad on a brake shoe, comprising the steps of:
   providing an ultrasonic wave (80) to the brake shoe (72) for transmission through the shoe to a boundary (82) for reflection in part as a first echo wave (82) and for transmission in part through the brake pad to a boundary (84) for reflection as a second echo wave (90);
   timing the time of transmission of the first echo wave (82) for determining the brake temperature; and
   timing the time of transmission of the second echo wave (90) for determining pad wear.

4. Brake sensing apparatus, comprising:
   an oscillator (270) for providing an oscillatory signal (272, 272a);
   a buffer (274), responsive to the oscillatory signal and to a start signal (276), for providing an excitation pulse (286, 286a);
   an ultrasonic transducer (264) attached to the brake shoe, responsive to the excitation pulse, for sensing and providing a pair of sensed echo signals (286b, 286c);
   an amplifier (294), responsive to the sensed echo signals and to an inverse start signal, for providing amplified echo signals only in the presence of the inverse start signal;
   a band pass filter (296), responsive to the amplified echo signals, for providing filtered echo signals (298);
   a comparator (300), responsive to the filtered echo signals and to a reference signal (302), for forming and providing echo pulse signals (304);
   an integrator (306), responsive to the echo pulse signal, for providing integrated echo pulse signals (308, 308a);
   first, second and third AND gates (310, 312, 314), each responsive to the amplified echo pulse signals and respectively responsive to first, second and third window signals (280, 280a; 282, 282a; 284, 284a), for respectively providing first, second and third stop signals (316, 318, 320);
   a pulse generator (278), for providing the start signal and the first, second and third window signals; and
   first, second and third timers (322, 324, 326), all responsive to the start signal for commencing timing upon reception thereof and respectively responsive to the first, second and third stop signals for providing timing output signals (328, 330, 332) respectively indicative of brake temperature, brake pad wear and on/off brake status.

5. The apparatus of claim 4, further comprising a computer (334), responsive to the timing output signals, for providing a speed signal (338).

6. The apparatus of claim 4, further comprising a computer (334), responsive to the timing output signals, for providing a pad wear signal (340).

7. The apparatus of claim 4, further comprising a computer (334), responsive to the timing output signals, for providing a brake status signal (342).

8. Apparatus, for sensing a brake having rotating radial indicia (150), comprising:
   an oscillator (164) for providing an oscillatory signal (106);
   a buffer (168), responsive to the oscillatory signal, for providing a buffered oscillatory signal (170, 170a);
   a first ultrasonic transducer (172), responsive to the buffered oscillatory signal, for providing an ultrasonic wave for transmission through the brake;
   a second ultrasonic transducer (174), responsive to the transmitted ultrasonic wave, for providing a sensed signal (176, 176a) modulated by the radial indicia;
   an amplifier (178), responsive to the sensed signal for providing an amplified sensed signal (180);
   a band pass filter (182), responsive to the amplified sensed signal, for providing band pass filtering (186, 186a);

an amplitude demodulator (188), responsive to the band pass signal, for providing a demodulated signal (190); and a frequency counter (192), responsive to the demodulated signal, for providing a speed signal (194) having a magnitude indicative of the angular velocity of the rotating radial indicia.

9. The apparatus of claim 8, further comprising:

a comparator (196), responsive to the band pass signal and to a reference signal (198) having a magnitude indicative of a wet brake condition, for providing a brake failure signal (204, 204a).

10. The apparatus of claim 8, further comprising:

a comparator (206), responsive to the band pass signal and to a reference signal (208) having a magnitude indicative of a brake engaged condition, for providing a brake engaged signal (214, 214a).

11. The apparatus of claim 8, further comprising:

a low pass filter (184), responsive to the amplified sensed signal (180), for providing a low pass filtered signal (216, 216a);

a comparator (218), responsive to the low pass filtered signal and to a reference signal (220) having a magnitude indicative of a brake drag condition, for providing a conditional brake failure signal; and an AND gate (228), responsive to the conditional brake failure signal and to an inverted brake engaged signal (232), for providing a brake failure signal (234).

12. A speed sensing method for a rotating brake drum or disc having radial indicia and having a brake pad associated therewith, comprising the steps of:

providing an ultrasound wave to the brake pad for amplitude modulation by the rotating indicia;

sensing the amplitude modulated ultrasound wave and providing a sensed signal having a magnitude indicative thereof; and amplitude demodulating the sensed signal for providing a demodulated signal having a magnitude indicative of the speed of the rotating drum or disc.

13. Speed sensing apparatus for a rotating brake drum or disc having radial indicia and having a brake pad associated therewith, comprising:

means for providing an ultrasound wave to the brake pad for amplitude modulation by the radial indicia;

means for sensing the amplitude modulated ultrasound wave for providing a sensed signal having a magnitude indicative thereof; and means for amplitude demodulating the sensed signal for providing a demodulated signal having a magnitude indicative of the speed of the rotating drum or disc.

* * * * *